US012600778B2

(12) United States Patent
Xu et al.

(10) Patent No.: US 12,600,778 B2
(45) Date of Patent: Apr. 14, 2026

(54) RAGE ANTIBODIES, FRAGMENTS AND USES THEREOF

(71) Applicants: The Research Foundation for The State University of New York, Amherst, NY (US); The Regents of the University of California, Oakland, CA (US)

(72) Inventors: Ding Xu, East Amherst, NY (US); Jeffrey Esko, La Jolla, CA (US); Miaomiao Li, Tonawanda, NY (US)

(73) Assignees: The Research Foundation for The State University of New York, Amherst, NY (US); The Regents of the University of California, Oakland, CA (US)

( * ) Notice: Subject to any disclaimer, the term of this patent is extended or adjusted under 35 U.S.C. 154(b) by 1018 days.

(21) Appl. No.: 17/772,853

(22) PCT Filed: Nov. 2, 2020

(86) PCT No.: PCT/US2020/058554
§ 371 (c)(1),
(2) Date: Apr. 28, 2022

(87) PCT Pub. No.: WO2021/087462
PCT Pub. Date: May 6, 2021

(65) Prior Publication Data
US 2022/0396618 A1      Dec. 15, 2022

Related U.S. Application Data

(60) Provisional application No. 63/027,235, filed on May 19, 2020, provisional application No. 62/928,884, filed on Oct. 31, 2019.

(51) Int. Cl.
| | |
|---|---|
| *C07K 16/28* | (2006.01) |
| *A61K 39/00* | (2006.01) |
| *A61K 47/68* | (2017.01) |
| *A61P 1/16* | (2006.01) |
| *A61P 19/10* | (2006.01) |
| *A61P 35/00* | (2006.01) |

(52) U.S. Cl.
CPC ...... *C07K 16/2803* (2013.01); *A61K 47/6811* (2017.08); *A61P 1/16* (2018.01); *A61P 19/10* (2018.01); *A61P 35/00* (2018.01); *A61K 2039/505* (2013.01); *C07K 2317/565* (2013.01); *C07K 2317/73* (2013.01); *C07K 2317/92* (2013.01)

(58) Field of Classification Search
CPC .......... C07K 16/2803; C07K 2317/565; C07K 2317/73; C07K 2317/92; C07K 2317/24; C07K 2317/33; C07K 2317/76; A61K 47/6811; A61K 2039/505; A61P 1/16; A61P 19/10; A61P 35/00
See application file for complete search history.

(56) References Cited

U.S. PATENT DOCUMENTS

| | | | |
|---|---|---|---|
| 2017/0226228 A1 | 8/2017 | Desir et al. | |
| 2017/0246315 A1 | 8/2017 | Conlan et al. | |
| 2018/0171029 A1 | 6/2018 | Harris et al. | |
| 2022/0177598 A1* | 6/2022 | Trinh ...................... | A61P 35/00 |

FOREIGN PATENT DOCUMENTS

WO      WO-2011122011 A2 *  10/2011  ............. C07K 16/28

OTHER PUBLICATIONS

Xu D, et al. Stable RAGE-heparan sulfate complexes are essential for signal transduction. ACS Chem Biol. Jul. 19, 2013;8(7):1611-20. doi: 10.1021/cb4001553. Epub May 28, 2013. PMID: 23679870; PMCID: PMC3806902. (Year: 2013).*

Brown M, et al. Tolerance of single, but not multiple, amino acid replacements in antibody VH CDR 2: a means of minimizing B cell wastage from somatic hypermutation? J Immunol. May 1, 1996;156(9):3285-91. PMID: 8617951. (Year: 1996).*

Vajdos FF, et al. Comprehensive functional maps of the antigen-binding site of an anti-ErbB2 antibody obtained with shotgun scanning mutagenesis. J Mol Biol. Jul. 5, 2002;320(2):415-28. doi: 10.1016/S0022-2836(02)00264-4. PMID: 12079396. (Year: 2002).*

Falconer R, et al. Stabilization of a monoclonal antibody during purification and formulation by addition of basic amino acid excipients. Journal of Chemical Technology and Biotechnology. 86. 942-948. 10.1002/jctb.2657. 2011 (Year: 2011).*

Tomita M, et al. Hybridoma technologies for antibody production. Immunotherapy. Mar. 2011;3(3):371-80. doi: 10.2217/imt. 11.4. PMID: 21395379. (Year: 2011).*

Xu, D., et al., Stable RAGE-Heparan Sulfate Complexes Are Essential for Signal Transduction, ACS Chemical Biology, May 16, 2013, vol. 8, No. 7, pp. 1611-1620.

Mizumoto, S., et al., Receptor for Advanced Glycation End Products (RAGE) Functions as Receptor for Specific Sulfated Glycosaminoglycans, and Anti-RAGE Antibody or Sulfated Glycosaminoglycans Delivered in Vivo Inhibit Pulmonary Metastasis of Tumor Cells, Journal of Biological Chemistry, Jun. 2012, vol. 287, No. 23, pp. 18985-18994.

* cited by examiner

Primary Examiner — Misook Yu
Assistant Examiner — Alec Jon Peters
(74) Attorney, Agent, or Firm — Hodgson Russ LLP

(57) ABSTRACT

Provided are antibodies specific for the heparan sulfate binding site of Receptor for Advanced Glycation Endproducts (RAGE). Also provided are methods for treating of conditions in which RAGE is involved comprising administration of the antibodies to an individual in need of treatment.

4 Claims, 8 Drawing Sheets

Specification includes a Sequence Listing.

A
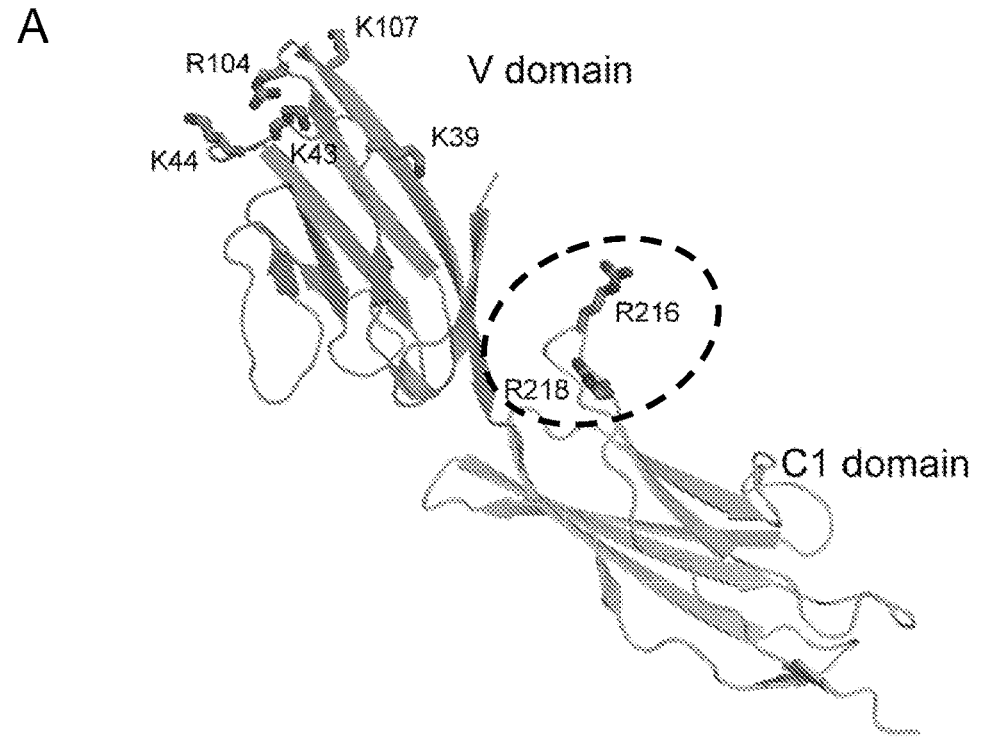
B
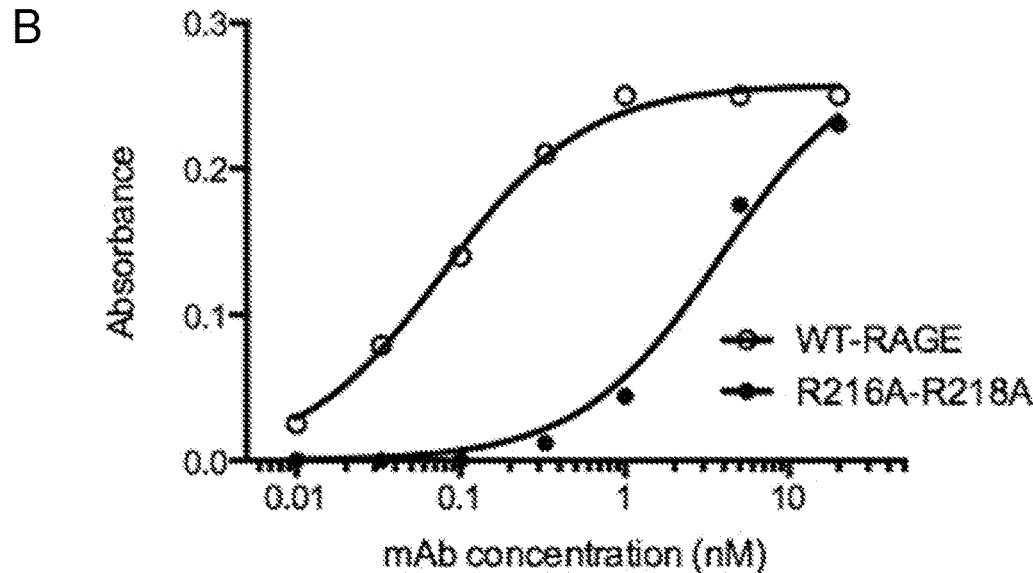
Fig. 1

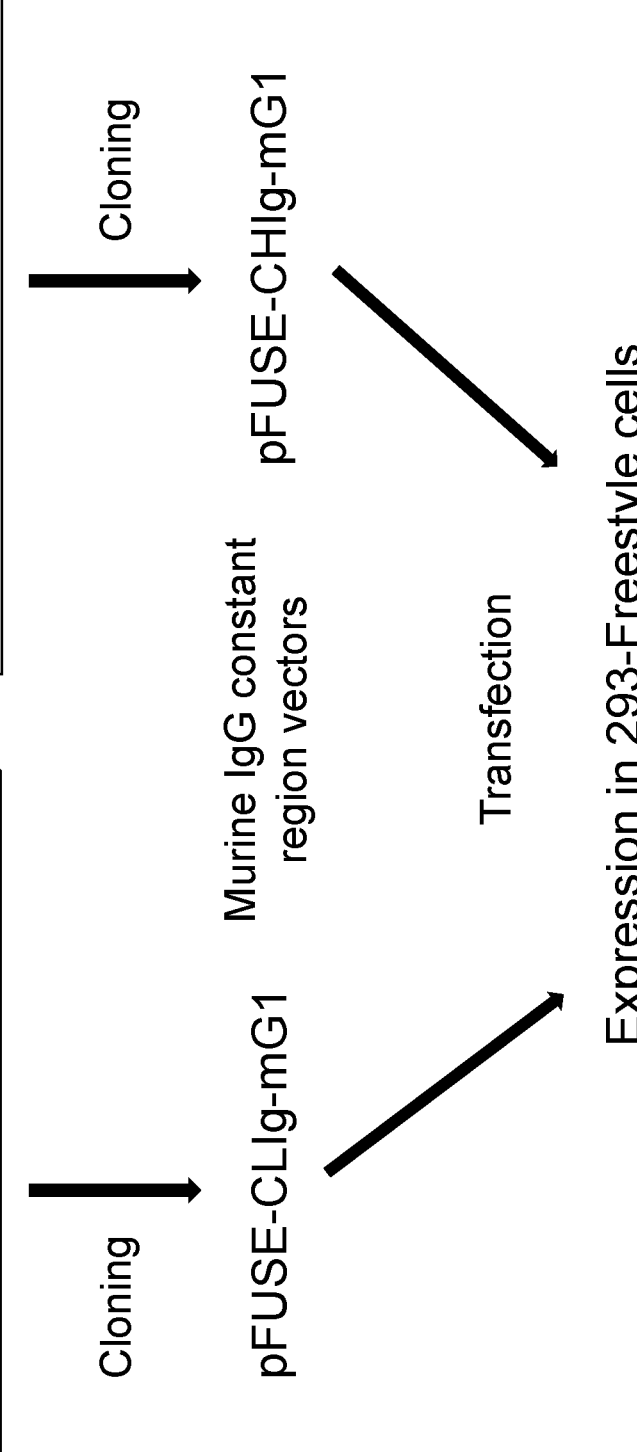

B2 light chain variable region

MDTRAPTQLLGLLLLWLPGATFAQVLTQTASPVSAAV
GSTVTINCQASQNVYDNNHLSWYQQKRGQPPKLLIY
YASALASGVSSRFKGSGSGTQFTLTINDVQCDDAAT
YYCLGSYDCSADCFAFGGGTEVVV (SEQ ID NO: 7)

B2 heavy chain variable region

METGLRWMLLVALLVAVLKGVQCQSVKESEGGLFKPTDTLT
LTCTVSGFTISSYDMSWVRQAPGKGLEWIGAIDSSG
SAHYASWARSRSTITRNTNLNTVTLKMTSLTAADTAT
YFCWNANIWGPGTLVTVSS (SEQ ID NO: 8)

Cloning → pFUSE-CLIg-mG1

Cloning → pFUSE-CHIg-mG1

Murine IgG constant
region vectors

Transfection

Expression in 293-Freestyle cells

Fig. 2

A
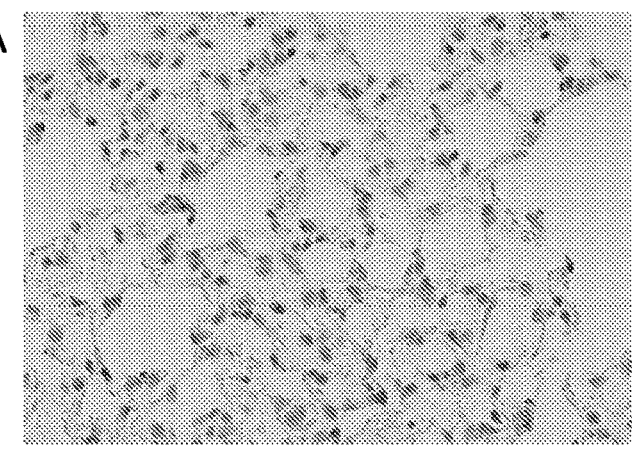
ctrl-IgG on WT lung
B
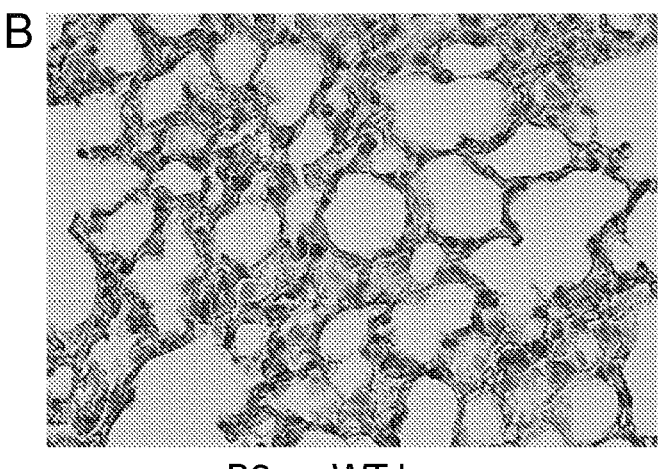
B2 on WT lung
C
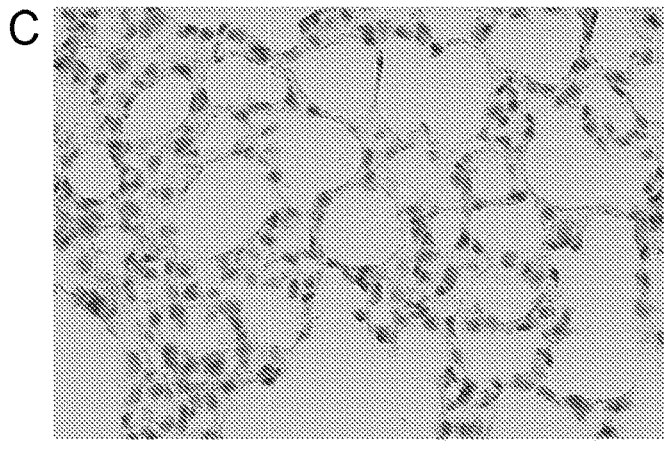
B2 on *Rage*⁻/⁻ lung
Fig. 3

A
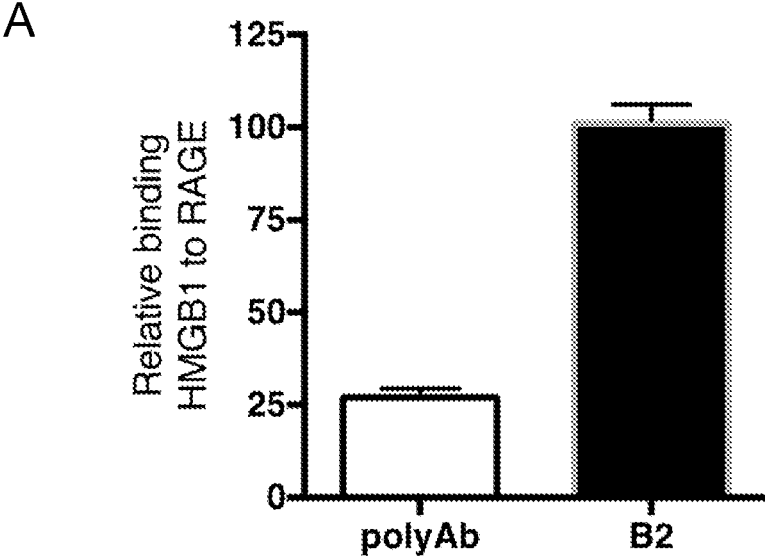
B
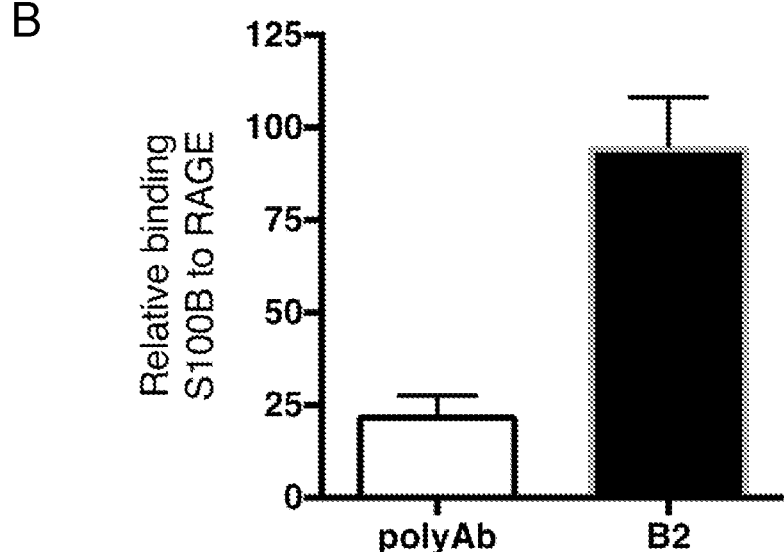
Fig. 4

RAGE ANTIBODIES, FRAGMENTS AND USES THEREOF

CROSS-REFERENCE TO RELATED APPLICATIONS

This application claims priority to U.S. Provisional patent application No. 62/928,884, filed on Oct. 31, 2019, and to U.S. Provisional patent application No. 63/027,235, filed on May 19, 2020, the disclosures of each of which are incorporated herein by reference.

STATEMENT REGARDING FEDERALLY-SPONSORED RESEARCH OR DEVELOPMENT

This invention was made with government support under Grant No. HL107150 awarded by the National Institutes of Health. The government has certain rights in the invention.

BACKGROUND OF THE DISCLOSURE

The Receptor for Advanced Glycation Endproducts (RAGE), a widely expressed receptor, has been shown to play a negative role in many pathological conditions such as drug-induced liver injury, sepsis, atherosclerosis, diabetes, cancer, Alzheimer's disease and periodontitis. The interaction between RAGE and its ligands is believed to lead to inflammation. RAGE exists in multiple isoforms such as fl-RAGE, N-RAGE, and sRAGE. RAGE is a unique receptor in that it binds to a wide spectrum of ligands. Known ligands of RAGE include advanced glycation endproducts (AGE), HMGB1, S100 proteins, amyloid-β-protein and lysophosphatidic acid. In different pathophysiological contexts, it is known that different ligands or combination of ligands activate RAGE. Animal studies using a variety of disease models have shown that genetically knocking out RAGE or pharmacologically blocking RAGE activation greatly improves disease outcome.

Soluble RAGE (sRAGE) has been shown to be an effective inhibitor of RAGE signaling (Bucciarelli et al., *Circulation* 106, 2827-2835 (2002), Park et al., *Nature medicine* 4, 1025-1031 (1998), Taguchi et al., Nature 405, 354-360 (2000). Pharmacologically, sRAGE works as a decoy receptor that competes with endogenous transmembrane RAGE for ligand binding. However, using sRAGE as a therapeutic agent may have some significant drawbacks due to the promiscuous nature of its ligands. Many ligand of RAGE, such as S100B and HMGB1, also interact with receptors other than RAGE (Riuzzi et al., *Journal of cell science* 124, 2389-2400 (2011), Park et al., *J. Biol. Chem.* 279, 7370-7377 (2004), Liu et al., *Mol. Pharmacol.* 74, 371-378 (2008), Ivanov et al., *Blood* 110, 1970-1981 (2007). Thus, neutralizing RAGE ligands with sRAGE may have broad and complex consequences on many other signal transduction pathways. It can be expected that the widespread effect of sRAGE would lower its safety profile and increase the chance of side effects. Another common strategy of inhibiting RAGE signaling is to target the ligand binding site of RAGE. Although several small molecules have been discovered that competitively inhibit RAGE-ligand interactions (Sabbagh et al., *Blood* 110, 1970-1981 (2011), Deane et al., *The Journal of clinical investigation* 122, 1377-1392 (2012), it is very unlikely that one small molecule would inhibit all, or even most, of the RAGE ligands. This is due to the fact that the binding sites for different RAGE ligands are not identical (Kierdorf et al., *J. Leukoc. Biol.* 94, 55-68 (2013).

In addition, competitive inhibitors often suffer from mass-action competition with the ligand (Swinney et al., *Nature reviews. Drug discovery* 3, 801-808 (2004). When the ligand concentration rises, such as during a disease state, the $IC_{50}$ value of the competitive inhibitor increases accordingly. This translates into reduced drug efficacy and therapeutic window.

SUMMARY OF THE DISCLOSURE

The present disclosure provides compositions and methods for inhibition of RAGE activation and signaling. The disclosure provides isolated antibodies, including monoclonal and polyclonal antibodies and fragments and variants thereof that are specific for the heparan-binding site of RAGE. The disclosure provides compositions comprising the antibodies, nucleic acid molecules encoding the antibodies or portions thereof or variants thereof, vectors comprising the nucleic acid molecules, cells comprising the antibodies and/or nuclei acid molecules, kits comprising one or more antibodies or nucleic acid molecules, and methods of using the antibodies or nucleic acid molecules or cells comprising the antibodies or nucleic acid molecules to inhibit RAGE activation and signaling.

In one aspect, the disclosure provides an isolated antibody, which may be a polyclonal or a monoclonal antibody (mAb), which is specifically reactive against the HS binding site of RAGE. The antibody may be generated in response to administration of a RAGE or a peptide thereof or a modification thereof.

An antibody of this disclosure can be a monoclonal antibody comprising a variable light chain (VL) and/or a variable heavy chain (VH), wherein the VL comprises CDRL1, denoted by the sequence NVYDNNHLS (SEQ ID NO: 1); CDRL2, denoted by the sequence LLIYYASALA (SEQ ID NO: 2); and CDRL3, denoted by the sequence LGSYDCSADCFA (SEQ ID NO: 3); and the VH comprises CDRH1, denoted by the sequence CTVSGFTISSYDM (SEQ ID NO: 4); CDRH2, denoted by the sequence AID-SSGSAH (SEQ ID NO: 5); and CDRH3, denoted by the sequence WNAN (SEQ ID NO: 6), wherein the antibody is specific for heparan sulfate (HS)-binding site of RAGE.

The antibodies of the present disclosure may be chimeric, human, or humanized antibodies. In a chimeric or humanized antibodies, some portions of the heavy and/or light chains may be identical or homologous to sequences from one species while other portions may be identical or homologous to sequences from a different species. For example, murine or rabbit monoclonal antibodies may be isolated or generated and then portions of these antibodies (or sequence information derived therefrom) used for generating chimeric or humanized antibodies. For example, rabbits may be immunized with RAGE or RAGE peptides and then ascites fluid samples can be collected. The samples can be screened and selected to develop a panel of monoclonal antibodies and corresponding hybridoma cell lines. Portions or sequences from the monoclonal antibodies can then be used to generate chimeric or humanized antibodies. An antibody of the present disclosure can also be an antibody fragment, a single chain, a bispecific or multispecific antibody.

The disclosure provides nucleic acid molecules comprising sequences encoding portions or all of the antibodies (including mAbs) sequences. The disclosure also provides cells comprising the nucleic acid molecules.

This disclosure provides a method of treatment of a condition associated with RAGE or abnormal RAGE function. Conditions in which RAGE function is abnormal or altered include atherosclerosis, arthritis, congestive heart failure, Alzheimer's disease, diabetes, myocardial infraction, peripheral vascular disease, psoriasis, sepsis, cancer, osteoporosis, periodontitis, tumors and drug-induced liver toxicity, and cancer. The method comprises administering to an individual afflicted with a condition in which RAGE function is altered a therapeutically effective amount of one or more antibodies that are specific for the heparin binding site of RAGE.

BRIEF DESCRIPTION OF THE FIGURES

FIG. 1 shows that rabbit B2 mAbs specifically bound to part of the HS-binding site of RAGE. Panel A shows residues that contributed to the HS-RAGE interactions are located in both the V and the C1 domain of RAGE. As shown in the dashed oval, the epitope of B2 mAb includes R216 and R218. Panel B depicts the binding of B2 mAbs to immobilized WT human RAGE or the R216A-R218A mutant as determined by ELISA. The binding of B2 mAbs to R216A-R218A was reduced by 40-fold. Without being bound by any theory, this suggests that R216 and R218 are part of the epitope recognized by B2 mAbs.

FIG. 2 presents the amino acid sequence of the variable region of B2 mAb that was sequenced and cloned into the mouse IgG backbone. The CDRs of both heavy and light chains are indicated in bold. Without being bound by any theory, residues that are believed to be the critical residues (D=aspartic acid) for B2-RAGE interaction are underlined. The B2 mAb light chain variable region and heavy chain variable region were cloned into pFUSE-CLIg-mG1 and pFUSE-CHIg-mG1 vectors to be expressed as rabbit-mouse IgG1 chimeric antibody. The chimeric B2 mAb was produced in 293-F cells by transient expression.

FIG. 3 shows that B2 mAbs bound to RAGE with high specificity. The paraffin embedded murine lung sections from wildtype BL/6 mouse (Panels A and B) or from Rage$^{-/-}$ mouse (Panel C) were immunostained with 1 μg/ml control murine IgG1 (Panel A) or mouse B2 IgG (Panels B and C). The WT lung demonstrated strong staining of RAGE, illustrated by the intense staining in Panel B by B2. In contrast, the lung section from Rage$^{-/-}$ mouse showed no staining by B2 (Panel C).

FIG. 4 illustrates that the binding of B2 mAbs does not affect RAGE binding to its ligand. Panel A shows the binding of biotinylated soluble RAGE (sRAGE) to immobilized HMGB1. The binding was measured in the presence of anti-RAGE rabbit polyclonal Ab or rabbit B2 mAb at 5 μg/ml. The level of binding of the sRAGE to HMGB1 in the absence of antibodies is defined as 100%. Panel B shows the binding of the biotinylated soluble RAGE (sRAGE) to immobilized S100b. The binding was measured in a similar fashion as described above.

DETAILED DESCRIPTION OF THE DISCLOSURE

Figure 5:
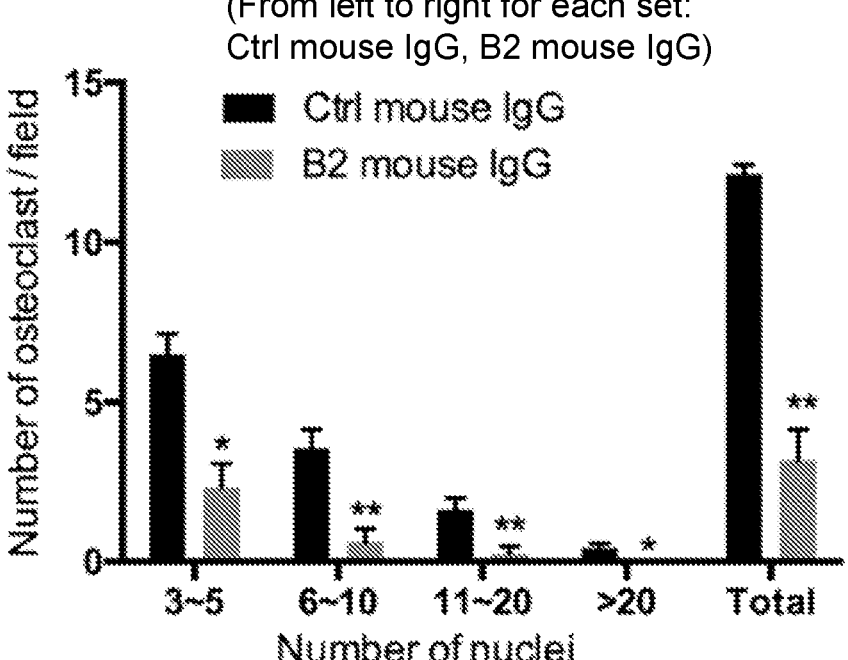
FIG. 5 depicts that B2 mAbs block osteoclast differentiation in vitro. Bone marrow macrophages were treated with M-CSF (10 ng/ml) and RANKL (50 ng/ml) for 7 days to induce osteoclastogenesis. The cells were incubated with either B2 mAbs or control mouse IgG at 20 μg/ml. The number of multinucleated osteoclasts (classified according to their size) were quantified. The data are averages of triplicate determinations±S.D. The treatment with B2 mAbs reduced the total number of mature osteoclasts (regardless of size) by 75% and the number of large osteoclasts (with more than 5 nuclei) by 90%.

The present disclosure is based on the elucidation of HS-RAGE interactions and generation of antibodies that specifically target the HS binding of RAGE with high specificity.

Throughout this application, the use of the singular form encompasses the plural form and vice versa. For example, "a", or "an" also includes a plurality of the referenced items, unless otherwise indicated.

Where a range of values is provided in this disclosure, it should be understood that each intervening value to the tenth decimal place of the lowest value, and all intervening ranges, between the upper and lower limit of that range is also included, unless clearly indicated otherwise. The upper and lower limits from within the broad range may independently be included in the smaller ranges encompassed within the disclosure.

The term "therapeutically effective amount" as used herein refers to an amount of an agent sufficient to achieve, in a single or multiple doses, the intended purpose of treatment. Treatment does not have to lead to complete cure, although it may. Treatment can mean alleviation of one or more of the symptoms or markers of the indication. The exact amount desired or required will vary depending on the particular compound or composition used, its mode of administration, patient specifics and the like. Appropriate effective amount can be determined by one of ordinary skill in the art informed by the instant disclosure using only routine experimentation. Within the meaning of the disclosure, "treatment" also includes prophylaxis and treatment of relapse, as well as the alleviation of acute or chronic signs, symptoms and/or malfunctions associated with the indication. Treatment can be orientated symptomatically, for example, to suppress symptoms. It can be effected over a short period, over a medium term, or can be a long-term treatment, such as, for example within the context of a maintenance therapy. Administrations may be intermittent, periodic, or continuous.

This disclosure provides isolated antibodies and fragments or variants thereof directed to HS binding site of RAGE, isolated nucleic acid molecules encoding antibodies or fragments or variants thereof, cells producing antibodies or fragments or variants thereof, vectors or cells comprising nucleic acids encoding antibodies or fragments or variants thereof, compositions comprising any of the foregoing, methods of making any of the foregoing, and methods of using the antibodies and fragments thereof, or nucleic acid molecules in the treatment of conditions associated with RAGE. Also provided are conjugates of the antibodies, fragments and variants thereof and drugs—generally referred to as antibody-drug conjugates or ADCs.

In particular, in the present disclosure, HS-RAGE specific antibodies are used to block HS-RAGE interaction that is considered to prevent RAGE oligomerization and activation. It is considered that HS-RAGE interaction and RAGE oligomerization are required for RAGE signaling. Pharmacologically, the present strategy is different from the conventional strategy in terms of the molecular mechanism of action. By targeting the surfaces that are not involved in ligand binding, this strategy is non-competitive in nature. A significant advantage of a non-competitive inhibitor over a competitive inhibitor is that the $IC_{50}$ is unaffected by the ligand concentration. This is advantageous because it helps maintain efficacy at low drug concentrations. Since HS-dependent RAGE oligomerization appears to be required for all RAGE ligands, blocking HS-RAGE interactions may be a universal way to block RAGE signaling.

Based on the crystal structure of RAGE-HS hexameric complex that we solved (PDB: 4IM8), we previously performed site-directed mutagenesis studies and identified the HS-binding site of RAGE (Xu et al., *ACS Chem. Biol.* 8, 1611-1620, 2013). The HS-binding site of RAGE includes seven basic residues. Five of these are located in the V domain (K39, K43, K44, R104 and K107) and two are found in the C1 domain (R216 and R218) (FIG. 1A). Knowing the exact HS-binding site of RAGE allowed us to identify mAbs that specifically target that site. In the present disclosure, we focused on antibodies that target the HS-binding residues (R216 and R218) located on the C1 domain. We demonstrate that such antibodies have a low chance of interfering with ligand binding, which occurs on the V domain.

In an aspect, this disclosure provides antibodies that interfere with HS binding to RAGE. In an embodiment, the antibodies bind to HS binding site of RAGE. The antibodies of the present disclosure bind to the HS binding site of RAGE with high affinity. The antibodies may bind with a $K_D$ from 0.1 to 10 nM. In embodiments, the $K_D$ may be from 0.1 to 1 nM. In embodiments, the antibodies do not interfere with the binding of RAGE to its ligands, such as, S100B and HMGB1. In an embodiment, the antibodies do not interfere with the binding of RAGE to HMGB1, S100 proteins, amyloid-β-protein and lysophosphatidic acid. In embodiments, the present antibodies do not bind to site or sites where HMGB1, S100 proteins, amyloid-β-protein or lysophosphatidic acid bind to RAGE. In an embodiment, the disclosure provides an antibody that binds to the HS binding site of RAGE with an affinity of at least 5 nM $K_D$ (such as from 0.1 nM to 5 nM) and does not interfere with the binding of S100B and HMGB1, which can independently bind to RAGE at affinities of about 80 nM and 10 nM, respectively.

Figure 6:
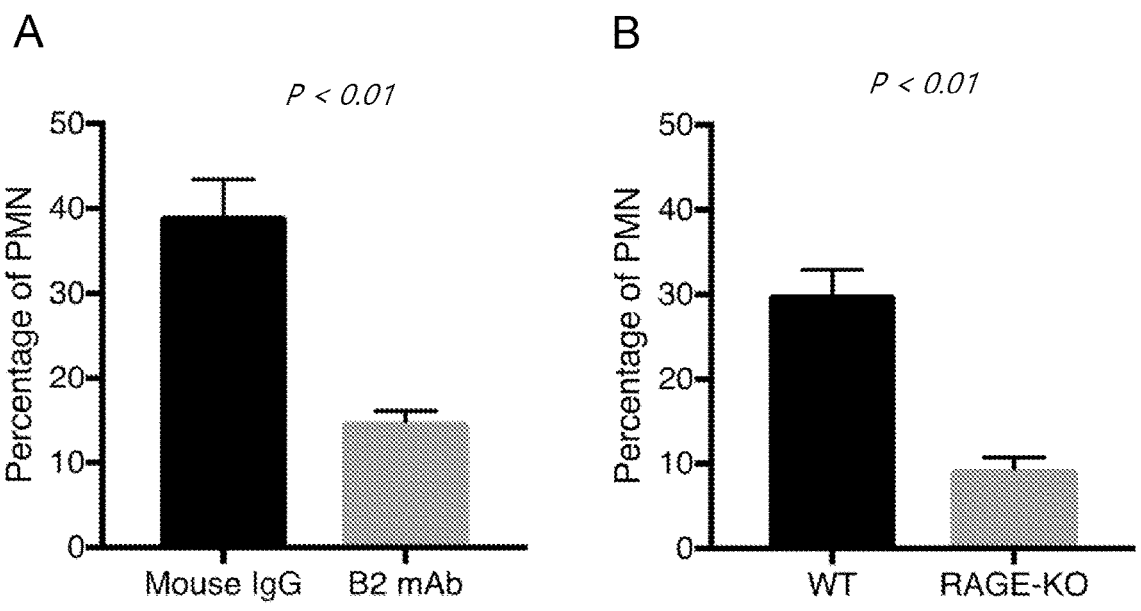
FIG. 6 depicts that B2 mAbs blocked liver lysate-induced neutrophil chemotaxis in vitro. Without being bound by any theory, this chemotaxis is believed to be RAGE-dependent. Panel A illustrates chemotaxis of bone-marrow derived murine polymorphonuclear leukocytes (PMNs or neutrophils) towards 30 mg of liver lysate using 5 transwells. Added to the bottom well were 10 μg/ml of B2 mAbs or control mouse IgG. The percentage of PMNs that migrated to the bottom wells were quantified by a hemocytometer. Panel B presents the chemotaxis assay comparing the wild-type PMNs versus the PMNs from Rage$^{-/-}$ mouse. We found a similar extent of reduction in the PMN chemotaxis by B2 mAb treatment (64% reduction) and by using RAGE-deficient PMNs (67% reduction).
Figure 7:
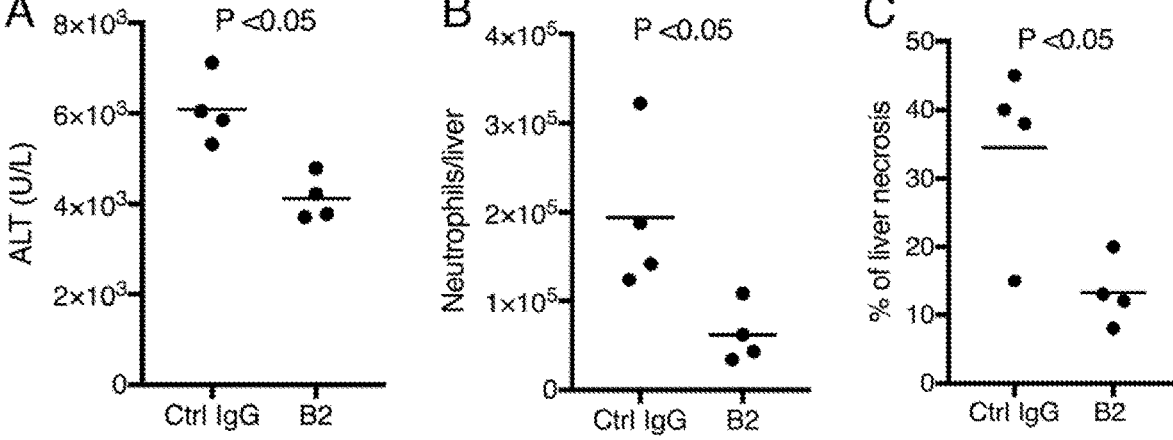
FIG. 7 shows that B2 mAbs were protective against acetaminophen-induced liver injury in vivo. The mice were injected with 250 μg of B2 mAbs or normal murine IgG 24 hours prior to the acetaminophen (APAP) injection. All of the mice were treated with 300 mg/kg APAP and sacrificed after 24 hours. The plasma level of alanine aminotransferase (ALT) levels were measured as an indicator of liver damage as shown in Panel A. The livers were harvested for the enumeration of neutrophils shown in Panel B and for histological examination of liver necrosis shown in Panel C.

In an embodiment, this disclosure provides a monoclonal antibody (mAb), termed herein as B2. This antibody bound to part of the heparan sulfate (HS)-binding site of RAGE with high specificity. B2 mAbs were able to block RAGE signaling in endothelial cells, neutrophils and osteoclasts. As shown in FIG. 5, B2 mAbs blocked RAGE-dependent osteoclastogenesis. As illustrated in FIG. 6, B2 mAbs blocked RAGE-dependent chemotaxis of neutrophils. B2 mAbs were also protective against acetaminophen-induced liver injury in vivo, as depicted in FIG. 7. Without being bound by any theory, it is considered that the mechanism of action of B2 mAbs involves blocking RAGE-HS interaction, which prevents RAGE activation. Our binding assay confirmed that B2 mAbs did not interfere with binding of RAGE to two common ligands, HMGB1 and S100b (FIG. 4).

FIG. 2 indicates the residues that are believed to be the complementarity determining regions (CDRs) of the B2 mAb heavy and light chains. 2. Based on alignment of the amino acid sequences of multiple rabbit mAbs, the critical residues that contribute to RAGE binding are likely the aspartic acid residues underlined in FIG. 2. These acidic residues may play a major role in binding to the basic residues on RAGE (arginine 216 and 218).

Thus, the subject invention provides an antibody or fragment or variant thereof comprising a light chain variable region having the sequence set forth in FIG. 2 and a heavy chain variable region having the sequence set forth in FIG. 2.

In addition, the subject invention provides antibodies or fragments thereof comprising a variable region in the light and/or heavy chain that is at least 85%, including all ranges and numbers (to 1 decimal place) between 85% and 99.9%, identical to the variable regions of the heavy and/or light chains in FIG. 2.

As used herein, "residue 1" refers to the 1st amino acid residue on the left. For example, "residue 1" of the light chain in FIG. 2 is M.

The subjection invention also provides an antibody or fragment thereof comprising a light chain variable region wherein residues 50-58 consist of NVYDNNHLS (SEQ ID NO: 1) and/or residues 70-79 consist of LLIYYASALA (SEQ ID NO: 2) and/or residues 113-124 consist of LGSYDCSADCFA (SEQ ID NO: 3) and/or comprising a heavy chain variable region wherein residues 40-52 consist of CTVSGFTISSYDM (SEQ ID NO: 4) and/or residues 68-76 consist of AIDSSGSAH (SEQ ID NO: 5) and/or residues 114-117 consist of WNAN (SEQ ID NO: 6). Without being bound by any theory, these residues are believed to be the complementarity-determining regions.

Furthermore, the subject invention provides antibodies or fragments thereof comprising a light chain variable region wherein residues 50-58 are least 85%, including all ranges and numbers (to 1 decimal place) between 85% and 99.9%, identical to NVYDNNHLS (SEQ ID NO: 1), and/or a light chain variable region wherein residues 70-79 are at least 85%, including all ranges and numbers (to 1 decimal place) between 85% and 99.9%, identical to LLIYYASALA (SEQ ID NO: 2), and/or a light chain variable region wherein residues 113-124 are at least 85%, including all ranges and numbers (to 1 decimal place) between 85% and 99.9%, identical to LGSYDCSADCFA (SEQ ID NO: 3), and/or a heavy chain variable region wherein residues 40-52 are at least 85%, including all ranges and numbers (to 1 decimal place) between 85% and 99.9%, identical to CTVSGFTIS-SYDM (SEQ ID NO: 4), and/or heavy chain variable region wherein residues 68-76 are at least 85%, including all ranges and numbers (to 1 decimal place) between 85% and 99.9%, identical to AIDSSGSAH (SEQ ID NO: 5), and/or heavy chain variable region wherein residues 114-117 are at least 85%, including all ranges and numbers (to 1 decimal place) between 85% and 99.9%, identical to WNAN (SEQ ID NO: 6).

In an embodiment, this disclosure provides antibodies that bind to and interfere with at least a part of the heparan sulfate (HS)-binding site of RAGE with high specificity, but does not interfere with RAGE-ligand binding. The CDRs of an exemplary antibody are described herein. In an embodiment, the antibody binds to a portion of RAGE that comprises arginines corresponding to (arginine 216 and 218 of RAGE).

In an embodiment, this disclosure provides antibodies that bind to the same epitope or region of RAGE as the antibody B2 described herein.

In an embodiment, this disclosure provides an antibody comprising a variable light chain (VL) and a variable heavy chain (VH), wherein the VL comprises CDRL1, denoted by the sequence NVYDNNHLS (SEQ ID NO: 1); CDRL2, denoted by the sequence LLIYYASALA (SEQ ID NO: 2); and CDRL3, denoted by the sequence LGSYDCSADCFA (SEQ ID NO: 3); and the VH comprises CDRH1, denoted by the sequence CTVSGFTISSYDM (SEQ ID NO: 4); CDRH2, denoted by the sequence AIDSSGSAH (SEQ ID NO: 5); and CDRH3, denoted by the sequence WNAN (SEQ ID NO: 6), wherein the antibody is specific for heparan sulfate (HS)-binding site of RAGE.

In an embodiment, this disclosure provides an antibody comprising a variable light chain (VL) and a variable heavy chain (VH), wherein the VL comprises CDRL1, denoted by the sequence NVYDNNHLS (SEQ ID NO: 1) or a sequence having at least 80%, 85% or 90% sequence identity with SEQ ID NO: 1, with the proviso that D is not substituted; CDRL2, denoted by the sequence LLIYYASALA (SEQ ID NO: 2) or a sequence having at least 80%, 85% or 90% sequence identity with SEQ ID NO: 2; and CDRL3, denoted by the sequence LGSYDCSADCFA (SEQ ID NO: 3) or a sequence having at least 80%, 85% or 90% sequence identity with SEQ ID NO: 3, with the proviso that neither of the Ds is substituted; and the VH comprises CDRH1, denoted by the sequence CTVSGFTISSYDM (SEQ ID NO: 4) or a sequence having at least 80%, 85% or 90% sequence identity with SEQ ID NO: 4, with the proviso that the D is not substituted; CDRH2, denoted by the sequence AIDSSGSAH (SEQ ID NO: 5), or a sequence having at least 80%, 85% or 90% sequence identity with SEQ ID NO: 5; and CDRH3, denoted by the sequence WNAN (SEQ ID NO: 6), or a sequence having at least 80%, 85% or 90% sequence identity with SEQ ID NO: 6, wherein the antibody is specific for heparan sulfate (HS)-binding site of RAGE.

In an embodiment, the antibody, comprises a variable light chain (VL) and a variable heavy chain (VH), wherein the sequence of the VL comprises MDTRAPTQLLGLLLL-WLPGATFAQVLTQTASPVSAAVGSTVTINCQASQN-VYDNNH LSWYQQKRGQPPKLLIYYASALASGVSS-RFKGSGSGTQFTLTINDVQCDDAATYYCL GSYDCSADCFAFGGGGTEVVV (SEQ ID NO: 7), or comprises a sequence that is at least 80, 85, 90, 95, 98 or 99% identical to SEQ ID NO: 7, and is specific for heparan sulfate (HS)-binding site of RAGE.

In an embodiment, the antibody, comprises a variable light chain (VL) and a variable heavy chain (VH), wherein the sequence of the VH comprises METGLRWLLLVA-VLKGVQCQSVKESEGGLFKPTDTLTLTCTVSGFTIS SYDMSWVR QAPGKGLEWIGAIDSSGSAHYASWAR-SRSTITRNTNLNTVTLKMTSLTAADTATYFC WNA-NIWGPGTLVTVSS (SEQ ID NO: 8), or comprises a sequence that is at least 80, 85, 90, 95, 98 or 99% identical to SEQ ID NO: 8, and is specific for heparan sulfate (HS)-binding site of RAGE.

The terms "antibody" as used herein can encompass whole antibody molecules, full-length immunoglobulin molecules, such as naturally occurring full-length immuno-globulin molecules or full-length immunoglobulin molecules formed by immunoglobulin gene fragment recombinatorial processes, as well as antibody fragments including scFvs. Antibody fragments can be fragments comprising at least one antibody-antigen binding site. Antibody fragments can, for example, exhibit specific binding to HS binding site of RAGE.

The term "antibody" can include e.g. monoclonal, poly-clonal, multispecific (for example bispecific), recombinant, human, chimeric and humanized antibodies. The term "anti-body" can also encompass recombinantly expressed antigen binding proteins and antigen binding synthetic peptides. Further, the term "antibody" as used herein encompasses minibodies, and diabodies, all of which preferably exhibit specific binding to HS binding site of RAGE, especially HD binding site of human RAGE. The term "antibody", as used herein, can also encompass antibodies produced in vivo, as well as those produced in vitro, such as, for example, by a bacterial expression system or a mammalian hybridoma cell line.

An antibody of the present disclosure may be modified by, for example, acetylation, formylation, amidation, phospho-rylation, or polyethylene glycolation (PEGylation), as well as glycosylation. The term "an antibody" as used herein is intended to cover all antibodies disclosed herein. For example, the term "an antibody" can refer to monoclonal, polyclonal, scFv, chimeric, human, or humanized antibodies, or antigen (i.e., HS binding portion of RAGE) binding fragments thereof. The fragments or other derivatized molecules (such as scFvs and the like) may generally be referred to as "antibodies" in this disclosure.

In an embodiment, the present antibodies are PEGylated to increase half-life and bioavailability. Various types of PEG molecules can be added to the antibodies, such as scFvs, including but not limited to PEG(5K), PEG(10K), PEG(20K), and PEG(40K). The antibodies or fragments, derivatives thereof, such as scFvs can be modified by the addition of a cysteine, lysine or serine amino acid to facilitate PEGylation. This modification can occur at, but is not limited to, the C-terminus of the antibodies.

The antibodies of the disclosure may be whole immuno-globulin molecules such as polyclonal or monoclonal anti-bodies or may be antigen-binding fragments thereof, including but not limited to, Fab, F(ab'), F(ab')2, Fv, dAb, Fd, CDR fragments, single-chain variable fragment antibodies (scFv), bivalent single-chain antibodies, single-chain phage anti-bodies, diabodies, nanobodies, BiKes, BiTes and the like. The fragments of the antibodies may be produced syntheti-cally or by enzymatic or chemical cleavage of intact immu-noglobulins or may be genetically engineered by recombi-nant DNA techniques. These techniques are well known in the art.

In one embodiment, this disclosure provides isolated antibodies. By the term "isolated" it is meant that the antibody or the fragment thereof, is separated and/or recov-ered from its natural environment. The isolation of the antibody from its natural environment can be such that the antibody can be used without interference from other active agents (such as other proteins) that normally are present in its natural environment.

In one embodiment, this disclosure provides generating and isolating single domain antibodies or nanobodies produced by camelids in response to introducing RAGE or RAGE peptides into the camelids. The nanobodies are typically heavy chain antibodies and thus contain heavy chain homodimers and do not contain antibody light chains. These antibodies typically comprise a single variable domain and two constant domains (CH2 and CH3).

The antibodies of the present disclosure may be obtained from a human or a non-human animal. In many mammals, intact immunoglobulins have two heavy chains and two light chains. Each of the light chains is covalently linked to a heavy chain by a disulfide bond. The two heavy chains are linked to each other by additional disulfide bonds. The light chain typically has one variable domain (VL) and one constant domain (CL). The heavy chain can also have one variable domain (VH). The variable domains contain complementarity-determining regions (CDRs). The heavy chain can further have three or four constant domains (CHI, CH2, CH3 and CH4). The variability of the constant domains results is various isotypes such as IgA, IgD, IgE, IgG, and IgM.

The CDRs are primarily responsible for binding to an epitope of an antigen. The CDRs of each chain are typically referred to as CDR1, CDR2, and CDR3, numbered sequentially starting from the N-terminus, and are typically identified by the chain in which the particular CDR is located. Thus, a $V_H$ CDR3 (referred to as VH-CDR3 or CDRH3) is located in the variable domain of the heavy chain of the antibody in which it is found, whereas a $V_L$ CDR1 (referred to as VL-CDR1 or CDRL1) is the CDR1 from the variable domain of the light chain of the antibody in which it is found. An antibody that binds to the HS binding site of RAGE, for example, will have a specific $V_H$ region and the $V_L$ region sequence, and thus specific CDR sequences. Antibodies with different specificities (i.e. different combining sites for different antigens) have different CDRs.

The terms $V_H$ or VH as used herein refer to the variable region of an immunoglobulin heavy chain, including a heavy chain of an Fv, scFv, dsFv or Fab, and the terms $V_L$ or VL refer to the variable region of an immunoglobulin light chain, including a light chain of an Fv, scFv, dsFv or Fab.

The term "monoclonal antibody" refers to an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. For example, mice, rabbits (or other suitable animals) may be immunized with RAGE or RAGE peptides and then ascites fluid samples can be collected. The samples can be screened and selected to develop a panel of monoclonal antibodies and corresponding hybridoma cell lines. Animal monoclonal antibodies may be isolated or generated and then humanized, if desired.

An antibody of the present disclosure can be an antibody of any class. For example, an antibody of the present invention can be an antibody isotype IgG1, IgG2, IgG3, IgG4, IgM, IgA, IgD or IgE. For example, the antibody can be IgG2b. The term "isotype", as used herein, can in particular refer to the antibody class (such as e.g. IgG) that is encoded by heavy chain constant region genes. Sequences of human immunoglobulin constant regions are known in the art and are available in public databases such as National Center for Biotechnology Information (NCBI), U.S. National Library of Medicine.

The term "chimeric antibody" refers to an antibody which has framework residues from one species, such as human, and CDRs (which generally confer antigen binding) from another species, such as a murine antibody that specifically binds the HS binding site of RAGE. In a chimeric antibody, some portions of the heavy and/or light chains may be identical or homologous to sequences from a particular species while other portions may be identical or homologous to sequences from a different species. Chimeric antibodies generally exhibit decreased immunogenicity and increased stability. Techniques for cloning murine immunoglobulin variable domains known in the art—such as, for example, see Orlandi et al., Proc. Natl Acad. Sci. USA 86: 3833 (1989), and Leung et al., Hybridoma 13:469 (1994). As an example of a chimeric antibody, polynucleotides encoding the variable domains of the light chain or the heavy chain of an antibody derived from an animal (e.g., mouse, rat, or chicken) other than human can be linked to polynucleotides encoding the constant domains of the light chain or the heavy chain derived from a human antibody to produce a polynucleotide (such as DNA) encoding a chimeric antibody.

A "human" antibody (also called a "fully human" antibody) is an antibody that includes human framework regions and all of the CDRs from a single or different human immunoglobulins. Thus, frameworks from one human antibody can be engineered to include CDRs from a different human antibody. Methods for producing human antibodies are known in the art—such as, for example, see Mancini et al., 2004, New Microbiol. 27:315-28; Conrad and Scheller, 2005, Comb. Chem. High Throughput Screen. 8:117-26.

A "humanized antibody" is typically a human antibody that has one or more amino acid residues imported into it (i.e., introduced into it) from a source that is non-human. For example, a humanized antibody is a recombinant protein in which the CDRs of an antibody from a species such as rodent, rabbit, dog, goat, or horse are imported into human heavy and light variable domains. The constant domains (also referred to as framework regions) of the antibody molecule are generally the same as those of a human antibody. The non-human immunoglobulin providing the CDRs can be termed as "donor" and the human immunoglobulin providing the framework can be termed as "acceptor". For example, all the CDRs can be from the donor immunoglobulin in a humanized immunoglobulin. Constant regions need not be always present, but if they are, they can be substantially identical to human immunoglobulin constant regions, i.e., at least about 85-90%, such as about 95% or more identical. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089, and U.S. Publication No. 2010/0196266). For example, murine monoclonal antibodies may be isolated or generated and then humanized. Examples of humanized antibodies include those comprising CDRs having sequences of SEQ ID NOs:1 through 6.

Antibody fragments can be produced by enzymatic digestion. For example, papain digestion of antibodies produces two identical antigen-binding fragments, called "Fab" fragments, and a "Fc" fragment. The Fab fragment contains an entire L chain and the variable region domain of the H chain (VH), and the first constant domain of one heavy chain. Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is capable of cross-linking antigen. "Fv" is the minimum antibody fragment that contains a complete antigen-recognition and -binding site and single-chain Fv also abbreviated as "sFv" or "scFv" are antibody fragments that comprise the VH and VL antibody domains connected into a single polypeptide chain. The term "diabodies" refers to small antibody fragments prepared by constructing sFv fragments with short linkers between the VH and VL domains such that interchain but not intra-chain pairing of the V domains is achieved, resulting in a bivalent fragment, i.e., fragment having two antigen-binding sites. A single domain antibody (sdAb) is an antibody fragment which has a single monomeric variable antibody domain. ScAbs can be made from heavy-chain antibodies found in camelids. An antibody fragment can be a single variable region or a peptide consisting of or comprising a single CDR. A single-chain antibody has a heavy chain variable domain and a light chain variable domain linearly linked to each other via a linker. A polynucleotide (such as DNA) encoding the single-chain antibody can be produced by binding a polynucleotide encoding the heavy chain variable domain, a polynucleotide encoding the linker (typically 10-20 nucleotides), and a polynucleotide encoding the light chain variable domain, with the heavy chain variable domain and the light chain variable domain being both derived from a human antibody.

The present disclosure also provides isolated nucleotide sequences encoding all or portions of the amino acid sequences disclosed herein. For example, the present disclosure provides an isolated nucleic acid molecule comprising the sequences of the CDRs, such as CDRL1, CDRL2, CDRL3, CDRH1, CDRH2, CDRH3 for the antibody as described in FIG. 2. In an embodiment, the present disclosure also provides isolated nucleic acid molecules comprising or consisting of the sequence encoding one or more CDRs described herein. The disclosure also provides cells comprising an expression vector or other polynucleotide sequence encoding the antibodies provided herein (including scFvs). Nucleotide sequences encoding the scFvs can be expressed using any suitable expression vector, many of which are known in the art and/or are commercially available. A vector generally includes nucleic acid sequences, such as origin or replication that enables it to replicate in a host cell. A vector can also include selectable marker genes.

The isolated monoclonal antibodies or fragments thereof can be labeled, such as with enzymatic, fluorescent or radioactive tags or can be conjugated to effector molecules such as, for example, toxins.

The disclosure provides cells comprising an expression vector or other polynucleotide sequence encoding the antibodies provided herein (including mAbs) or fragments that bind to HS-binding site of RAGE. Nucleotide sequences encoding the mAbs or fragments thereof that bind to HS-binding site of RAGE can be expressed using any suitable expression vector, many of which are known in the art and/or are commercially available. A vector generally includes nucleic acid sequences, such as origin or replication that enables it to replicate in a host cell. A vector can also include selectable marker genes. Heavy and light chains can be expressed on a single expression vector, such as a plasmid or the heavy and light chains can be expressed on distinct plasmids in the same cell, after which the expressed heavy and light chains can form the conventional mAb architecture. The mAbs or RAGE binding fragments thereof can be isolated and/or purified using conventional techniques, given the benefit of the present disclosure.

This disclosure provides compositions comprising antibodies, antibody fragments or derivatives loaded onto liposomes. Standard approaches for ligand attachment to aqueous liposome nanoparticles make use of maleimides, succinimidyl esters and carbodiimide-activated carboxylic acids. These can covalently react with amine and thiol groups of polypeptides. The use of maleimide-lipids has been explored extensively for antibody-conjugated liposomes. Conjugation yields may reach as high as 90% from an overnight reaction, but subsequent quenching of free maleimide groups and additional purification is required. Proteins may require a preparative step of thiolation and purification prior to conjugation. Antibody orientation is a major factor influencing the conjugated antibody target binding efficacy, but these approaches result in numerous antibody labeling sites and indiscriminate orientations. Biorthogonal synthetic strategies such as the click reaction have recently been applied to pre-formed liposomes, however these require the use exogenous catalysts and unconventional amino acids.

The liposomes in the present disclosure may be spherical or non-spherical. The size of the liposomes can be from 50 to 1000 nm or more. In one embodiment, the liposomes have a size (e.g., a longest dimension such as, for example, a diameter) of 50 to 1000 nm, including all integer nm values and ranges therebetween. For example, the size may be from 50 to 200 nm or from 20 to 1000 nm. If the liposomes are not spherical, the longest dimension can be from 50 to 1000 nm. These dimensions can be achieved while preserving the nanostructure width of the monolayer or the bilayer. The liposomes can carry cargo in the aqueous compartment. The cargo, or part thereof, can also, or alternatively, be incorporated in the monolayer or the bilayer.

In an embodiment the present antibodies, fragments or derivatives can be used in conjunction with cytotoxic drugs, such as in the form of antibody drug conjugates. For example the antibodies, fragments, or derivatives may be conjugated to campothecin, calicheamicin, maytansinoid, auristatin E (MMAE), pyrrolobenzodiazepine, or a derivative, analog or metabolite of any of the aforementioned drugs. The drugs may be anti-tumor drugs or drugs that inhibit the growth of cells.

In addition, the subjection invention provides an antibody or fragment thereof comprising a light chain variable region wherein one or more of residues 53, 117 or 121 is D and/or comprising a heavy chain variable region wherein residue 51 is D. Without being bound by any theory, these residues are believed to be the critical residues.

As used herein, antibody fragments include, but are not limited to, scFv, Fab, F(ab')2, F(ab'), scFab, scFV-CH, scFV-Fc, scFv-zipper (2 scFvs connected by long linkers such as leucine zippers), diabodies (db), scDb, triabodies, tetrabodies and minibodies.

Either l- or d-amino acids may be used in the invention. In certain embodiments, conservative substitutions of the amino acids are contemplated. The term, "conservative substitution," is used to reflect amino acid substitutions that do not substantially alter the activity (e.g., antifungal activity and/or specificity) of the molecule. Typically, conservative amino acid substitutions involve substitution of one amino acid for another amino acid with similar properties (e.g. charge, hydrophobicity and size). Conservative substitutions include, but are not limited to Gly/Ala; Arg/Lys; Ser/Tyr/Thr; Leu/Ile/Val; Asp/Glu; Gln/Asn; and Phe/Trp/Tyr. Other examples of substitutions within the scope of the invention include: Gly/Ala/Pro; Tyr/His; Arg/Lys/His; Ser/Thr/Cys; and Leu/Ile/Val/Met.

Substitution can also be in the form of analog substitutions where a standard amino acid is replaced by a non-standard amino acid such as a synthetic or rare amino acid differing minimally from the parent residue from which it is typically derived. Some examples of amino acid analogs are: beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methyl-valine, norvaline, norleucine, and ornithine.

The antibodies and fragments retain their ability to bind the HS binding site of RAGE.

In an embodiment, the antibody or fragment thereof is monoclonal. Optionally, the antibody or fragment thereof may be polyclonal.

In certain embodiments, the antibody or fragment thereof may be fully or partially humanized.

The subject invention further includes nucleic acid sequences encoding the antibodies or fragments thereof. These nucleic acid sequences may be incorporated into vectors. The nucleic acids or vectors may be incorporated into host cells.

The present disclosure provides antibody-drug conjugates (ADCs). Any antibody, fragment, variant or derivative described here may be used. It may be conjugated, directly or via a linker, to a drug. Examples of drugs are those that can inhibit the growth if cells, such as cancer cells. Examples of drugs include campothecin, calicheamicin, maytansinoid, auristatin E (MMAE), pyrrolobenzodiazepine, or a derivative, analog or metabolite of any of the aforementioned drugs.

The present disclosure provides pharmaceutical compositions comprising the antibodies or fragments thereof, or ADCs and pharmaceutically suitable carrier. Suitable carriers include excipients, or stabilizers which are nontoxic to recipients at the dosages and concentrations employed, and include buffers such as acetate, Tris, phosphate, citrate, and other organic acids; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; and/or non-ionic surfactants such as Tween or polyethylene glycol (PEG). The pharmaceutical compositions may comprise other therapeutic agents.

Compositions of the present disclosure can comprise one type of monoclonal antibody or more than one type of monoclonal antibody. A composition of the disclosure can have one or more of an antibody or fragment or variant thereof. A composition can have a monoclonal and a polyclonal antibody. A composition can comprise one or more subtypes of antibodies. For example, a composition can comprise a mixture of IgG or IgM or a mixture of one or more of IgG1, IgG2, and IgG2b. A composition of the present disclosure can comprise an antibody as the only active ingredient, wherein the antibody may be monoclonal, polyclonal, chimeric, human, humanized or combinations thereof. By "active ingredient" is meant that the ingredient can interfere with binding of HS and RAGE, such as by binding to the HS-binding site of RAGE.

The subject invention provides a method of treating a subject afflicted with a disease or condition associated with altered RAGE signaling by administering to the subject a therapeutically effective amount of the antibodies or fragments thereof, or antibody-drug conjugates. A disease or condition is associated with RAGE or altered RAGE signaling when symptoms of the disease or condition are ameliorated by inhibition of RAGE. Non-limiting examples of diseases or conditions associated with RAGE include atherosclerosis, arthritis (including rheumatoid arthritis), Takayasu's arthritis, congestive heart failure, Alzheimer's disease, diabetes (including diabetic nephropathy, diabetic retinopathy and diabetic neuropathy), myocardial infraction, peripheral vascular disease, psoriasis, sepsis, cancer, osteoporosis, periodontitis, tumors and drug-induced liver toxicity. It is considered that RAGE plays a prominent role in the afore-mentioned pathophysiological conditions.

Additionally, the subject invention provides a method of treating a subject afflicted with a disease associated with altered RAGE function or signaling, such as, but not limited to, atherosclerosis, arthritis (including rheumatoid arthritis), Takayasu's arthritis, congestive heart failure, Alzheimer's disease, diabetes (including diabetic nephropathy, diabetic retinopathy and diabetic neuropathy), myocardial infraction, peripheral vascular disease, psoriasis, sepsis, cancer, osteoporosis, periodontitis, a tumor and/or drug-induced liver injury by administering to the subject a therapeutically effective amount of the antibodies or fragments thereof. In an embodiment, an individual who is at risk of developing a condition, such as arthritis or osteoporosis may be administered the present compositions. In an embodiment, an individual who has developed a pre-condition, such as osteopenia, pre-diabetes, pre-arthritis and the like may be administered the present compositions to halt or delay the progression of disease.

In an embodiment, the present disclosure provides a method for treatment of bone disorder comprising administering to an individual who is in need of treatment a therapeutically effective amount of a present antibody, fragment or variant. The bone disorder may be osteoporosis or osteopenia, or bone loss may be caused by trauma or surgery. The present antibody may inhibit bone resorption or may enhance bone regeneration or both.

Drug-induced liver injury (DILI) is associated with prescription medications, over the counter drugs (OTC) and herbal and dietary supplements. Specific drugs and classes associated with DILI include: allopurinol, amiodarone, amoxicillin-clavulanate, anabolic steroids, androgen-containing steroids, anti-TNF agents, azathioprine, carbamazepine, flavocoxid, fluoroquinotones, green tea extract, inhaled anesthetics, interferon-alfa, interferon-beta, isoni-azid, lamotrigine, macrolides, methotrexate—oral, minocy-cline, nitrofurantoin, NSAIDs, phenytoin, proton pump inhibitors, pyrrolizidine alkaloids, sulfasalazine, TMP-SMX, and valproate. In the United States, antibiotics and antiepileptic drugs are the most common drug classes asso-ciated with DILI.

In an embodiment, the present disclosure provides a method for reducing drug induced liver injury, wherein the method comprises administering to an individual who is also being administered a drug that is associated with DILI, an effective amount of a present antibody or an antibody, fragment or modification thereof. The antibody of the pres-ent disclosure may be administered prior to, concurrently, or sequentially with the drug associated with DILI, and may be administered over the same or different periods of time, via same or different routes. An effective amount as used in this disclosure refers to an amount that will result in the intended effect. For example an effective amount to reduce drug induced liver injury is the amount of the present antibodies that will result in reduced liver injury compared to if the drug is administered without the antibody regimen.

In an embodiment, the disclosure provides a method of inhibiting the growth of cancer cells. The disclosure pro-vides a method of treating an individual afflicted with a cancer, comprising administering to an individual in need of treatment a therapeutically effective amount of an antibody, fragment or modification thereof, or an antibody-drug con-jugate thereby reducing tumor growth. Examples of cancers that may be treated with the present compositions include blood cancers as well as tumors. Examples of tumors include but are not limited to, prostate cancer, testicular cancer, pancreatic cancer, lung cancer, which may be non-small cell lung cancer (NSCLC), which may be squamous cell (or epidermoid) carcinoma, adenocarcinoma and, large cell (or undifferentiated) carcinoma, or any other type, melanoma of the skin, kidney cancer, bladder cancer, liver cancer, colon cancer, head and neck cancers, breast cancer, ovarian cancer, cervical cancer, Hodgkin lymphoma, urinary tract cancers, and other types of cancers. The cancer, such as lung cancer or breast cancer may be refractory to current treatments. The breast cancer may be metastatic triple-negative breast can-cer, all stages, and may be refractory to current treatments. Individuals who may receive the present compositions may include those who have already undergone other types of therapies, including chemotherapy, surgical intervention, or hormonal therapy and the like.

The subject may be an animal, such as a human or other mammal.

A pharmaceutical composition of the disclosure can com-prise one or more antibodies at a concentration range from 0.1 mg/ml to 100 mg/ml, 1 mg/ml to 10 mg/ml, 1 mg/ml to 50 mg/ml, 1 mg/ml to 100 mg/ml, 10 mg/ml to 100 mg/ml, or 50 mg/ml to 100 mg/ml of each of the antibodies or total antibodies. For example, a pharmaceutical composition of the disclosure can comprise at least or about 0.1 mg/ml, at least or about 1 mg/ml, at least or about 5 mg/ml, at least or about 10 mg/ml, at least or about 50 mg/ml, at least or about 100 mg/ml of an antibody.

The compositions of the present disclosure may be admin-istered by routine methods known in the art. For example, the compositions comprising antibodies or fragments thereof may be administered via intravenous, intramuscular, intraperitoneal, intracerebrospinal, subcutaneous, intra-ar-ticular, intrasynovial, intrathecal, oral, topical, or inhalation routes, or by intracerebral or intra-spinal convection enhanced delivery or direct intratumoral injection. The antibodies may be administered parenterally directly at the target site (such as at or within a tumor). The compositions may be introduced as a single administration or as multiple administrations and may be introduced in a continuous manner over a period of time. In one embodiment, the composition may be administered daily for a period of at least 2 days such as, for example, for a period of 2-30 days (and all periods therebetween). In one embodiment, it is administered daily for 7-10 days. It may alternatively be administered at desired intervals (such as every 2, 3, 4, 5 days and the like).

It will be recognized by those of skill in the art that the form and character of the particular dosing regimen employed in the method of the invention will be dictated by the route of administration and other well-known variables, such as the size of the individual and the stage of the disease. Further, the compositions can be provided in the form of unit dosage forms for administration to an individual in need of treatment. Antibodies can be provided in a lyophilized form to be reconstituted prior to administration. The reconstitu-tion medium can be sterile 0.9% saline solution or a suitable physiological buffer or water, or any other solution known in the art for reconstituting proteins prior to administration.

The disclosure also provides kits which can be used for administration to individuals in need of treatment. A kit, for example, can comprise one or more antibodies, which may be in a lyophilized form, optionally reconstitution media, and instructions for administration. A kit can comprise a single dose or multiple doses.

The following examples are meant to illustrate, and are not intended to be limiting.

Example 1

Results

We have identified a mAb (B2) that specifically binds to part of the HS-binding site located at the C1 domain (FIG. 1A). B2 mAbs have high affinity to both murine and human RAGE (apparent $K_d$ to murine and human RAGE were 0.03 nM and 0.08 nM, respectively based on ELISA). Without being bound by any theory, the binding of B2 mAbs appears to rely on amino acid residues R216 and R218, as shown in FIG. 1B.

To produce B2 mAbs in large quantity for in vivo studies and to avoid potential immunological response to rabbit mAb, we cloned the variable regions of B2 from hybridoma cells and grafted them onto murine $IgG_1$ constant region. The sequence of the variable regions revealed that B2 mAbs contain many aspartic acids in the regions that appear to be the complementarity determining regions, without being bound by any theory. This is consistent with the basic epitopes that they recognize (FIG. 2). To fuse the variable regions of the B2 mAb heavy and light chains onto mouse $IgG_1$ constant regions, they were cloned into pFUSE-CHIg-mG1 and pFUSE-CLIg-mG1 (Invivogen) vectors, respec-tively. The recombinant mAbs, which were transiently expressed in 293-freestyle cells, fully retained their epitope specificity and affinity. The expression level of B2 mAbs was also excellent, consistently yielding approximately 20 mg of mAbs from one liter of shaker culture.

To verify the specificity, we performed lung tissue stain-ing using B2 mAbs (FIG. 3). B2 mAbs strongly stained the plasma membranes of cells from the WT lung, whereas none of the cells were stained in the lung tissue prepared from Rage$^{-/-}$ mice. This showed that B2 mAbs possessed excel-lent specificity for RAGE and the likelihood that they cross-reacted with another mouse protein was slim to none.

Biochemical characterization of B2 mAbs showed that binding of B2 mAbs to RAGE did not interfere with the binding of its ligands, HMGB1 and S100B, whereas rabbit polyclonal anti-RAGE antibody substantially inhibited the binding of both ligands (FIG. 4). Without being bound by any theory, this demonstrates that B2 mAbs bound the C1 domain of RAGE, whereas the vast majority of ligands bound the V domain of RAGE.

To determine the biological activity of B2 mAbs, we performed in vitro assays to examine their effect on osteo-clastogenesis and neutrophil migration. In the osteoclasto-genesis assay, B2 mAbs significantly reduced the number of total osteoclasts to 30% of control level, with a most dramatic effect on preventing the formation of larger osteo-clasts with more than 6 nuclei (FIG. 5). In neutrophil chemotaxis assay, neutrophils treated with B2 mAbs showed greatly reduced migration towards liver lysate, a process known to be dependent on interaction between HMGB1 (abundant in liver lysate) and RAGE expressed by neutro-phils (FIG. 6A). Of note, the effect of B2 mAbs in this assay likely represents the maximum effect achievable by blocking RAGE pathway, as neutrophils isolated from RAGE-KO mice showed a similar extent of residual neutrophil migra-tion (FIG. 6B).

We also performed an in vivo experiment to examine the efficacy of B2 mAbs in alleviating acetaminophen-induced liver injury. Our results showed that B2 mAbs were able to significantly reduce ALT level, neutrophil infiltration and liver necrosis by 40-60%. These findings suggest that B2 mAbs were effective in protecting mice from liver damage in vivo (FIG. 7).

Figure 8:
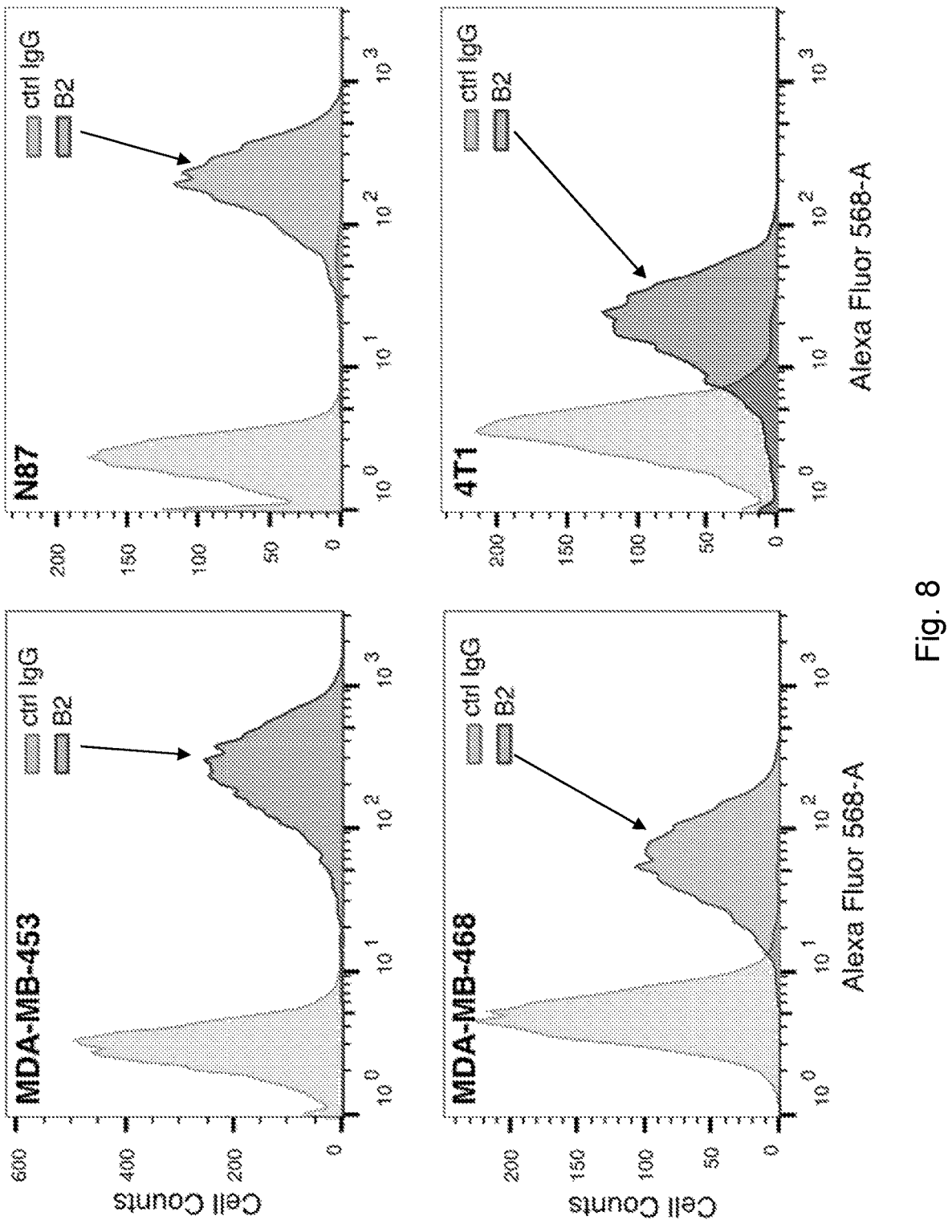
FIG. 8. B2 binds to cell surface RAGE expressed by tumor cells. Human breast cancer lines (MDA-MB-453 and MDA-MB-468), murine breast cancer line 4T1 and human gastric tumor line N87 were incubated with 120 nM of human chimeric B2 or human control IgG, followed by incubation with Alexa568-conjugated anti-human IgG. The binding was analyzed by flow cytometry.
Figure 9:
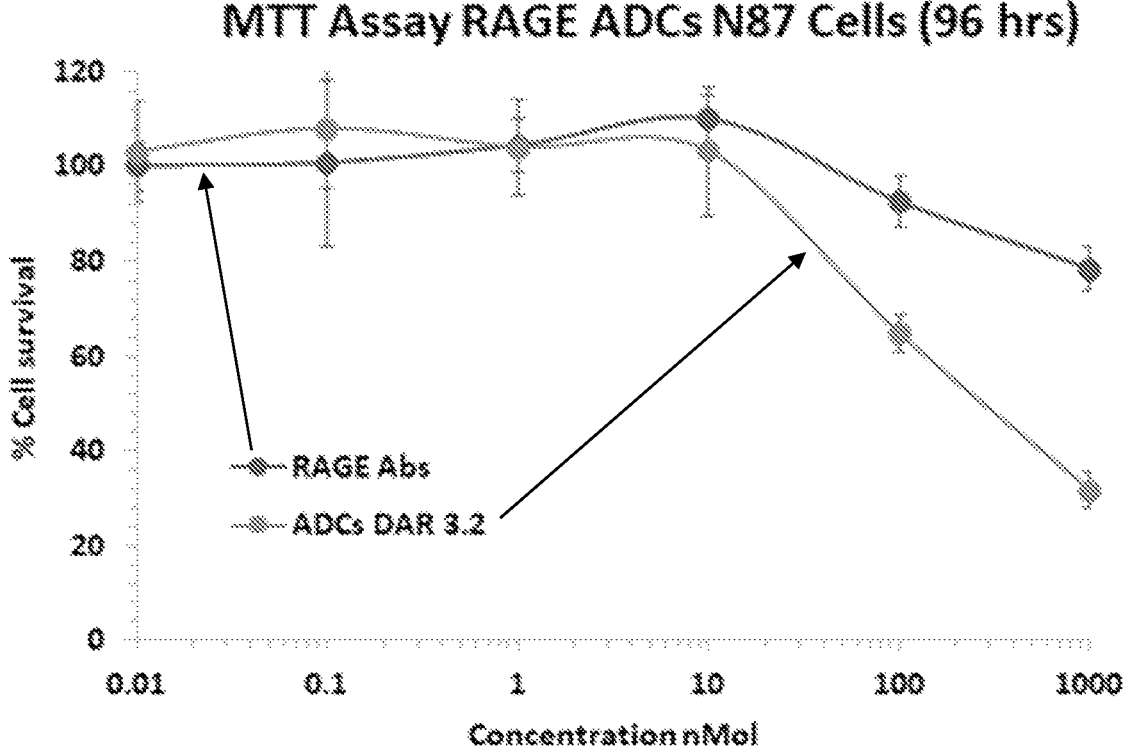
FIG. 9. B2-based antibody-drug conjugate (ADC) is effective in killing tumor cells. Anti-RAGE mAb B2 was conjugated to vc-MMAE with drug:antibody ratio around ~3. NCI-N87 gastric tumor cells were incubated with different concentrations of ADC for 96 h, and cell viability was quantified at the end of the experiment. Unconjugated antibody was used as a control.

Using B2, we show here that two human breast tumor cell lines, one murine breast tumor cells line and one human gastric tumor line express high level of RAGE (FIG. 8). This result suggest that B2 might be used as an antibody-drug-conjugate to specifically target RAGE-expression tumor cells. Indeed, we found that when conjugated to a common cytotoxicity drug vc-MMAE, B2-based ADC was effective in killing NCI-N87 cells (FIG. 9).

Materials and Methods

Production of B2 mAbs

The rabbit monoclonal antibodies (mAbs) were raised against the receptor for advanced glycation end-products (RAGE) in Dr. Jefferey Esko's lab at UC San Diego. The hybridoma line of rabbit used was 240 E-W3. The rabbits were immunized with murine RAGE V-C1 domain (mVC1) in its native conformation. The rabbit hybridomas were generated at Epitomics (now part of Abcam). Out of the 4,000 hybridoma clones that were screened, around 100 were able to detect mVC1 by direct ELISA. The supernatant of the positive clones were then screened in our lab for mAbs that specifically interacted with the HS-binding site. In this screening, instead of using WT mVC1, various mVC1 mutants (K43A-K44A, K39A-R104A, K107A, and R216A-R218A) were immobilized to ELISA plates. These mutants bear alanine mutations in the HS-binding residues. In this assay, mAbs were sought that show reduced binding to the mutants compared to the WT mVC1. In principle, the reduced binding would only occur if the residues that we mutated belong to the epitope recognized by the mAb.

Identification of the Epitope for B2 mAb by ELISA 200 ng of human RAGE extracellular domain or R216A-R218A mutant were immobilized onto 96-well high-binding ELISA plate. Plates were blocked with 5% BSA in PBS and incubated with 0.01 to 10 nM of rabbit B2 mAb for 1 hour at room temperature. Bound B2 mAbs were quantitated with anti-rabbit-HRP (Jackson Immunology) followed by the addition of HRP substrate (Thermo Scientific).

Sequencing and Cloning of B2 mAb

To obtain the coding sequences of the heavy and light chains of the B2 mAb, we used a 5'-RACE method. Rabbit hybridoma clone expressing B2 was reverse transcribed use a 5'-RACE kit (Thermofisher) and PCR amplified, which was eventually cloned into a vector and sequenced to obtain coding sequences of the variable regions of heavy and light chains. The variable regions were than grafted onto murine IgG$_1$ constant region by cloning into pFUSE-CHIg-mG1 and pFUSE-CLIg-mG1 (Invivogen) vectors, respectively. The recombinant mAbs, which were transiently expressed in 293-freestyle cells, fully retained their epitope specificity and affinity.

Effect of B2 on Ligand Binding to RAGE

HMGB1 or S100b (200 ng) were immobilized and the plate was blocked as described above. Biotinylated-mouse B2 V-C1 domain (200 ng/ml) was pre-incubated with rabbit IgG, polyclonal or monoclonal anti-RAGE (all at 5 μg/ml) for 30 minutes at room temperature before being added to the plate. Quantification of binding was performed as described above. The percentage of antibody inhibition was calculated by comparing the absorbance obtained in the presence of specific antibodies to the absorbance obtained in the presence of control rabbit IgG.

Determination of the Specificity of B2 Using Lung Sections

Paraffin sections of lung tissues of WT and Rage-/- mice were stained with 1 μg/ml murine-rabbit chimeric B2 or control mouse IgG1 and developed using DAB peroxidase substrate kit (Vector Lab). Cell nuclei were counterstained with hematoxylin (represented in black in FIG. 3). In the figure, dark grey shading indicates staining of RAGE.

Effect of B2 mAbs on Osteoclastogenesis

Bone marrow macrophages isolated from murine femur and tibia were treated with M-CSF and RANKL (Peprotech Inc) for 5 days to induce osteoclastogenesis. Cells were incubated with either B2 mAbs or control mouse IgG at 20 μg/ml. Osteoclasts were fixed and visualized by a TRAP staining kit (Sigma-Aldrich). The number of multinucleated osteoclasts (classified according to their size) were quanti-fied using a inverted microscope.

Effect of B2 mAbs on Neutrophil Chemotaxis

Polymorphonuclear leukocytes (PMNs or neutrophils) were isolated from murine bone marrow by Percoll gradient. The purity of PMN was >95%. The chemotaxis assay was performed using 5 μm transwells (Corning). Approximately $3 \times 10^5$ PMNs in 100 μl of medium were added into the transwell inserts and 10 mg liver lysate was added into the bottom plate well. 10 μg/ml of B2 mAbs or control mouse IgG were also added into the bottom well. The transwells were incubated at 37° C. incubator for 2 hours to allow PMN chemotaxis. The percentage of PMNs that migrated to the bottom wells were quantified by hemocytometer.

Effect of B2 in Acetaminophen-Induced Liver Injury

All animal experiments were approved by the Institutional Animal Care and Use Committee of the University at Buffalo. 10-week old male C57BL/6J mice were purchased from Jackson laboratory (Bar Harbor, Maine). Mice were fasted overnight (12-15 h) before IP administration of 300 mg/kg APAP (Sigma). Mice were IP injected with 10 mg/kg murine B2 or control mouse IgG 24 hours prior to APAP injection. 24 hours post acetaminophen injection, mice were sacrificed by cardiac puncture and the livers were harvested. The pa level of ALT, a marker of hepatocytes necrosis, was measured by a commercial ALT assay kit (Thermo-Fisher).

As another way to examine the liver damage, one lobe of liver was fixed in 10% formalin for histology assessment of liver necrosis. To examine the inflammation states of the liver, another lobe of liver was minced and digested with collagenase to obtain single cell suspension. After removing hepatocytes by 33% Percoll gradient, the remaining cells (mostly leukocytes) were stained with anti-Ly6G for neutrophil quantification by flow cytometry.

Binding of B2 to tumor cells. ~3×10$^5$ tumor cells (human MDA-MB-453, MDA-MB-468 and NCI-N87, and murine 4T1) were incubated with 120 nM of human chimeric B2 or human control IgG for 15 min at room temperature, followed by incubation with Alexa568-conjugated anti-human IgG for 15 min. The binding was analyzed by flow cytometry (BD Biosciences).

Effect of B2-based ADC on killing tumor cells. Anti-RAGE mAb B2 was conjugated to vc-MMAE with drug: antibody ratio around ~3. NCI-N87 gastric tumor cells were incubated with 0.01 to 1000 nM of ADC for 96 hours, and cell viability was quantified at the end of the experiment by MTT assay. Unconjugated B2 was used as a control.

Screening of mAb Library

Rabbits were immunized with murine RAGE V-C1 domain (mVC1) in its native conformation and the rabbit that produced the best ELISA titer was used to isolate splenocytes for generating rabbit hybridomas. Out of 4,000 hybridoma clones that we screened, around 100 were able to detect mVC1 by direct ELISA. The supernatants of the positive clones were then screened for mAbs that specifically interacted with the HS-binding site. In this screen, instead of using WT mVC1, we immobilized various mVC1 mutants (K43A-K44A, K39A-R104A, K107A, and R216A-R218A) to ELISA plates. These mutants bear alanine mutations in the residues contribute to HS-binding. We screened the mAbs for reduced binding to the mutants compared to the WT mVC1. In principle, the binding would only be reduced if the mutated residues belong to the epitope recognized by the mAb. Using this method, we identified two mAbs with reduced binding to the HS-binding site. Due to its superior affinity (apparent Kd to mVC1 was 0.08 nM, respectively) and production level, as well as excellent cross-reactivity to human RAGE, we decided to focus on B2 mAbs.

Humanization of B2 mAbs

B2 mAbs can be humanized using a well-established CRD grafting technique. Briefly, the six CDR loops comprising the antigen-binding site of B2 are grafted into corresponding human framework regions. Then, computer modeling assists randomizing certain framework residues in addition to the CDR grafting. The grafted CDRs combined with the randomized residues are cloned into a phage display library and the humanized antibodies with the best affinity are selected by screening of the library. This approach retains the epitope specificity of the original antibody. Several companies offer a customized humanization service using the above-described CDR grafting technique.

This disclosure describes that Rabbit mAbs were raised against Receptor for advanced glycation end-products (RAGE), One mAb, termed B2, was found to specifically bind part of the heparan sulfate (HS)-binding site of RAGE. In depth study of B2 found it is able to blocking RAGE signaling in endothelial cells, neutrophils and osteoclasts. The variable region of rabbit mAb B2 was cloned and grafted onto mouse IgG constant region. The mouse version of B2 is recombinantly expressed in 293 cells. The mechanism of action of B2 involves blocking RAGE-HS interaction, which is essential for RAGE activation. Some features of the antibodies of the present disclosure include: Rabbit mAb B2 specifically binds the HS-binding site of RAGE; the variable region of B2 was sequenced and cloned into mouse IgG backbone; B2 binding does not affect RAGE binding to its ligand; B2 binds highly specifically to RAGE; B2 blocks RAGE-dependent osteoclastogenesis; B2 blocks RAGE-dependent neutrophils chemotaxis; B2 is protective against acetaminophen-induced liver injury in vivo.

Although the present disclosure has been described using specific embodiments and examples, routine modifications will be apparent to those skilled in the art and such modifications are intended to be within the scope of the disclosure and the claims.

40

What is claimed is:

1. An isolated antibody that binds to heparin sulfate binding site of Receptor for Advanced Glycation Endproducts (RAGE) on a cell and does not interfere with the binding of RAGE ligands to RAGE on the cell, said antibody comprising a variable light chain (VL) and a variable heavy chain (VH), and wherein CDRL1 comprises the sequence denoted in SEQ ID NO: 1, the CDRL2 comprises the sequence demoted by SEQ ID NO: 2, the CDRL3 comprises the sequence denoted by SEQ ID NO: 3, the CDRH1 comprises the sequence denoted by SEQ ID NO: 4, the CDRH2 comprises the sequence denoted by SEQ ID NO: 5, and the CDRH3 comprises the sequence denoted by SEQ ID NO: 6.

2. The isolated antibody of claim 1, wherein the antibody is a chimeric antibody, a humanized antibody, a single chain antibody, a bispecific antibody or a multispecific antibody.

3. The isolated antibody of claim 1, wherein the antibody has an isotype of IgG1, IgG2, IgG3, IgG4, IgM, IgA, IgD or IgE.

4. A pharmaceutical composition comprising an isolated antibody of claim 1 and a pharmaceutically acceptable carrier.

* * * * *

SEQUENCE LISTING

```
<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: CDR

<400> SEQUENCE: 1

Asn Val Tyr Asp Asn Asn His Leu Ser
1               5

<210> SEQ ID NO 2
<211> LENGTH: 10
<212> TYPE: PRT
<213> ORGANISM: Artificial Sequence
<220> FEATURE:
<223> OTHER INFORMATION: CDR

<400> SEQUENCE: 2

Leu Leu Ile Tyr Tyr Ala Ser Ala Leu Ala
1               5                   10
```

-continued

```
<210> SEQ ID NO 3
<211> LENGTH: 12
<212> TYPE: PRT
<213> ORGANISM: Artificial Sequence
<220> FEATURE:
<223> OTHER INFORMATION: CDR

<400> SEQUENCE: 3

Leu Gly Ser Tyr Asp Cys Ser Ala Asp Cys Phe Ala
1               5                   10

<210> SEQ ID NO 4
<211> LENGTH: 13
<212> TYPE: PRT
<213> ORGANISM: Artificial Sequence
<220> FEATURE:
<223> OTHER INFORMATION: CDR

<400> SEQUENCE: 4

Cys Thr Val Ser Gly Phe Thr Ile Ser Ser Tyr Asp Met
1               5                   10

<210> SEQ ID NO 5
<211> LENGTH: 9
<212> TYPE: PRT
<213> ORGANISM: Artificial Sequence
<220> FEATURE:
<223> OTHER INFORMATION: CDR

<400> SEQUENCE: 5

Ala Ile Asp Ser Ser Gly Ser Ala His
1               5

<210> SEQ ID NO 6
<211> LENGTH: 4
<212> TYPE: PRT
<213> ORGANISM: Artificial Sequence
<220> FEATURE:
<223> OTHER INFORMATION: CDR

<400> SEQUENCE: 6

Trp Asn Ala Asn
1

<210> SEQ ID NO 7
<211> LENGTH: 133
<212> TYPE: PRT
<213> ORGANISM: Artificial Sequence
<220> FEATURE:
<223> OTHER INFORMATION: VL chain

<400> SEQUENCE: 7

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Pro
            20                  25                  30

Val Ser Ala Ala Val Gly Ser Thr Val Thr Ile Asn Cys Gln Ala Ser
        35                  40                  45

Gln Asn Val Tyr Asp Asn Asn His Leu Ser Trp Tyr Gln Gln Lys Arg
    50                  55                  60

Gly Gln Pro Pro Lys Leu Leu Ile Tyr Tyr Ala Ser Ala Leu Ala Ser
65                  70                  75                  80

Gly Val Ser Ser Arg Phe Lys Gly Ser Gly Ser Gly Thr Gln Phe Thr
                85                  90                  95
```

-continued

```
Leu Thr Ile Asn Asp Val Gln Cys Asp Asp Ala Ala Thr Tyr Tyr Cys
            100                 105                 110

Leu Gly Ser Tyr Asp Cys Ser Ala Asp Cys Phe Ala Phe Gly Gly Gly
        115                 120                 125

Thr Glu Val Val Val
    130

<210> SEQ ID NO 8
<211> LENGTH: 129
<212> TYPE: PRT
<213> ORGANISM: Artificial Sequence
<220> FEATURE:
<223> OTHER INFORMATION: VH chain

<400> SEQUENCE: 8

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Thr Leu Thr Cys Thr Val Ser Gly Phe Thr Ile Ser
        35                  40                  45

Ser Tyr Asp Met Ser Trp Val Arg Gln Ala Pro Gly Lys Gly Leu Glu
    50                  55                  60

Trp Ile Gly Ala Ile Asp Ser Ser Gly Ser Ala His Tyr Ala Ser Trp
65                  70                  75                  80

Ala Arg Ser Arg Ser Thr Ile Thr Arg Asn Thr Asn Leu Asn Thr Val
                85                  90                  95

Thr Leu Lys Met Thr Ser Leu Thr Ala Ala Asp Thr Ala Thr Tyr Phe
            100                 105                 110

Cys Trp Asn Ala Asn Ile Trp Gly Pro Gly Thr Leu Val Thr Val Ser
        115                 120                 125

Ser
```